(12) United States Patent
Hirano et al.

(10) Patent No.: US 8,049,897 B2
(45) Date of Patent: Nov. 1, 2011

(54) RETICLE DEFECT INSPECTION APPARATUS AND INSPECTION METHOD USING THEREOF

(75) Inventors: Ryoichi Hirano, Tokyo (JP); Riki Ogawa, Kanagawa (JP)

(73) Assignees: Kabushiki Kaisha Toshiba, Tokyo (JP); NEC Corporation, Tokyo (JP)

( * ) Notice: Subject to any disclaimer, the term of this patent is extended or adjusted under 35 U.S.C. 154(b) by 689 days.

(21) Appl. No.: 12/047,844

(22) Filed: Mar. 13, 2008

(65) Prior Publication Data

US 2008/0259328 A1   Oct. 23, 2008

(30) Foreign Application Priority Data

Apr. 18, 2007   (JP) .................. 2007-109288

(51) Int. Cl.
*G01N 21/55* (2006.01)
(52) U.S. Cl. .................................... 356/447
(58) Field of Classification Search .................. None
See application file for complete search history.

(56) References Cited

U.S. PATENT DOCUMENTS

| 7,491,959 B2 * | 2/2009 | Ogawa et al. | 356/237.5 |
| 2002/0054283 A1 * | 5/2002 | Kato et al. | 356/400 |
| 2002/0060793 A1 * | 5/2002 | Fukui | 356/400 |
| 2004/0119959 A1 * | 6/2004 | Nishi | 355/53 |
| 2004/0252296 A1 * | 12/2004 | Tojo et al. | 356/237.5 |
| 2006/0018530 A1 * | 1/2006 | Oaki et al. | 382/144 |

FOREIGN PATENT DOCUMENTS

| JP | 63-173322 | | 7/1988 |
| JP | 03144305 A | * | 6/1991 |
| JP | 9-82605 | | 3/1997 |
| JP | 11-72905 | | 3/1999 |
| JP | 2006-98156 | | 4/2006 |

OTHER PUBLICATIONS

Japanese AIPN Online English Translation of JP H11-072905—Sep. 3, 2010.*
Japanese AIPN Online English Translation of JP H09-082605—Sep. 2, 2010.*

* cited by examiner

*Primary Examiner* — Gregory J Toatley
*Assistant Examiner* — Juan D Valentin
(74) *Attorney, Agent, or Firm* — Oblon, Spivak, McClelland, Maier & Neustadt, L.L.P.

(57) ABSTRACT

A reticle defect inspection apparatus that suppresses deterioration of optical components resulting from luminescent spots generated by an integrator and can sustain a defect inspection with high precision for a long time is provided. The reticle defect inspection apparatus is a reticle defect inspection apparatus for inspecting for defects on a reticle using a pattern image obtained by irradiating the reticle on which a pattern is formed with light. And the apparatus includes an illuminating optical system for irradiating the reticle with an inspection light and a detecting optical system for detecting a pattern image of the reticle irradiated with the inspection light, wherein the illuminating optical system comprises an integrator for equalizing illumination distribution of the inspection light and a moving mechanism for enabling the integrator to slightly move in a direction perpendicular to an optical axis of the integrator.

8 Claims, 7 Drawing Sheets

RETICLE DEFECT INSPECTION APPARATUS AND INSPECTION METHOD USING THEREOF

CROSS-REFERENCE TO RELATED APPLICATION

This application is based upon and claims the benefit of priority from Japanese Patent Application No. 2007-109288, filed on Apr. 18, 2007, the entire contents of which are incorporated herein by reference.

FIELD OF THE INVENTION

The present invention relates to a reticle defect inspection apparatus using an image obtained by irradiating a sample with light for inspection and an inspection method using thereof.

BACKGROUND OF THE INVENTION

Some patterns constituting a large-scale integrated circuit (LSI), as exemplified by DRAM of a gigabit class, have a minimum feature size on the order of submicron to nanometer. One of major causes for yield reduction in a manufacturing process of such an LSI includes defects on a reticle (also called a mask) used for lithography.

Particularly with increasingly finer pattern dimensions of LSI formed on a semiconductor wafer, dimensions that must be detected as pattern defects are also becoming extremely smaller. Thus, reticle defect inspection apparatuses with high resolution for inspecting for extremely small defects are vigorously being developed.

An effective method of improving resolution is to make wavelengths of inspection light shorter. Thus, DUV (Deep Ultra Violet) light sources providing short wavelengths are increasingly used as light sources for generating inspection light. In addition, it is desirable to obtain high-precision images in order to improve resolution and, for this purpose, it is necessary to irradiate a reticle with a uniform inspection light (or illumination light) using an illuminating optical system of a reticle defect inspection apparatus. To obtain such a uniform inspection light, an effective method is considered to provide an integrator (also called a homogenizer or fly eye lens) in the illuminating optical system (for example, JP-A. 2006-98156(KOKAI)). An integrator is constituted, for example, by bundling a plurality of rod lenses having a length of several dozen mm and a diameter of about 1 mm and a uniform inspection light can be realized by causing a laser light to pass through the integrator.

An object of the present invention is to provide a reticle defect inspection apparatus that can sustain a high-precision defect inspection for a long time and an inspection method using thereof.

SUMMARY OF THE INVENTION

A reticle defect inspection apparatus in accordance with a first aspect of the present invention is a reticle defect inspection apparatus for inspecting for defects on a reticle using a pattern image obtained by irradiating the reticle on which a pattern is formed with light and includes an illuminating optical system for irradiating the reticle with an inspection light and a detecting optical system for detecting the pattern image of the reticle irradiated with the inspection light, wherein the illuminating optical system includes: an integrator for equalizing illumination distribution of the inspection light; and a moving mechanism for enabling the integrator to slightly move in a direction perpendicular to an optical axis of the integrator.

A reticle defect inspection apparatus in accordance with a second aspect of the present invention is a reticle defect inspection apparatus for inspecting for defects on a reticle using a pattern image obtained by irradiating the reticle on which a pattern is formed with light and includes an illuminating optical system for irradiating the reticle with an inspection light and a detecting optical system for detecting the pattern image of the reticle irradiated with the inspection light, wherein the illuminating optical system includes: an integrator for equalizing illumination distribution of the inspection light; an optically transparent optical path change plate provided on an optical path on a side of the reticle of the integrator; and a moving mechanism for enabling the optical path change plate to tilt with respect to an optical axis of the integrator.

A reticle defect inspection method in accordance with an aspect of the present invention is an inspection method using a reticle defect inspection apparatus for inspecting for defects on a reticle using a pattern image obtained by irradiating the reticle on which a pattern is formed with light. The reticle defect inspection apparatus includes, an illuminating optical system for irradiating the reticle with an inspection light; and a detecting optical system for detecting the pattern image of the reticle irradiated with the inspection light. The illuminating optical system, includes: an integrator for equalizing illumination distribution of the inspection light; and a moving mechanism for enabling the integrator to slightly move in a direction perpendicular to an optical axis of the integrator, and the integrator is moved by a predetermined amount in a direction perpendicular to an optical axis of the integrator after performing a plurality of reticle defect inspections.

DETAILED DESCRIPTION OF THE EMBODIMENTS

If an integrator is used in an illuminating optical system, light fluxes generated after division by the integrator are condensed to generate an area (hereinafter also referred to as a luminescent spot surface) in the optical system in which luminescent spots (energy concentration) are formed. Such luminescent spots will be distributed repeatedly in the X and Y directions at certain intervals, that is, like lattice points on the luminescent spot surface. The inventors found that, if an optical component exists on the luminescent spot surface, the optical component will be irradiated with DUV light for a long time while irradiation energy is concentrated, leading to deterioration of the optical component.

If the optical component is an objective lens, for example, the deterioration manifests itself as deterioration of the transmittance. Then, when transmittance of the objective lens deteriorates, a problem arises that correct optical images cannot be obtained due to multiple images (so-called ghosts) or the like because optical image information is modulated by spatial frequencies based on the intervals of luminescent spots.

Embodiments of a reticle defect inspection apparatus that suppresses deterioration of optical components resulting from luminescent spots generated by an integrator and can sustain a defect inspection with high precision for a long time and an inspection method using thereof will be described with reference to drawings.

First Embodiment

A reticle defect inspection apparatus in the present embodiment is a reticle defect inspection apparatus that inspects for defects on a reticle using a pattern image obtained by irradiating the reticle on which patterns are formed with light. The reticle defect inspection apparatus has an illuminating optical system for irradiating a reticle with an inspection light and a detecting optical system for detecting a pattern image of the reticle irradiated with the inspection light. In addition, the illuminating optical system has an integrator for equalizing illumination distribution of the inspection light and a moving mechanism for enabling the integrator to move slightly in a direction perpendicular to the optical axis of the integrator.

Figure 2:
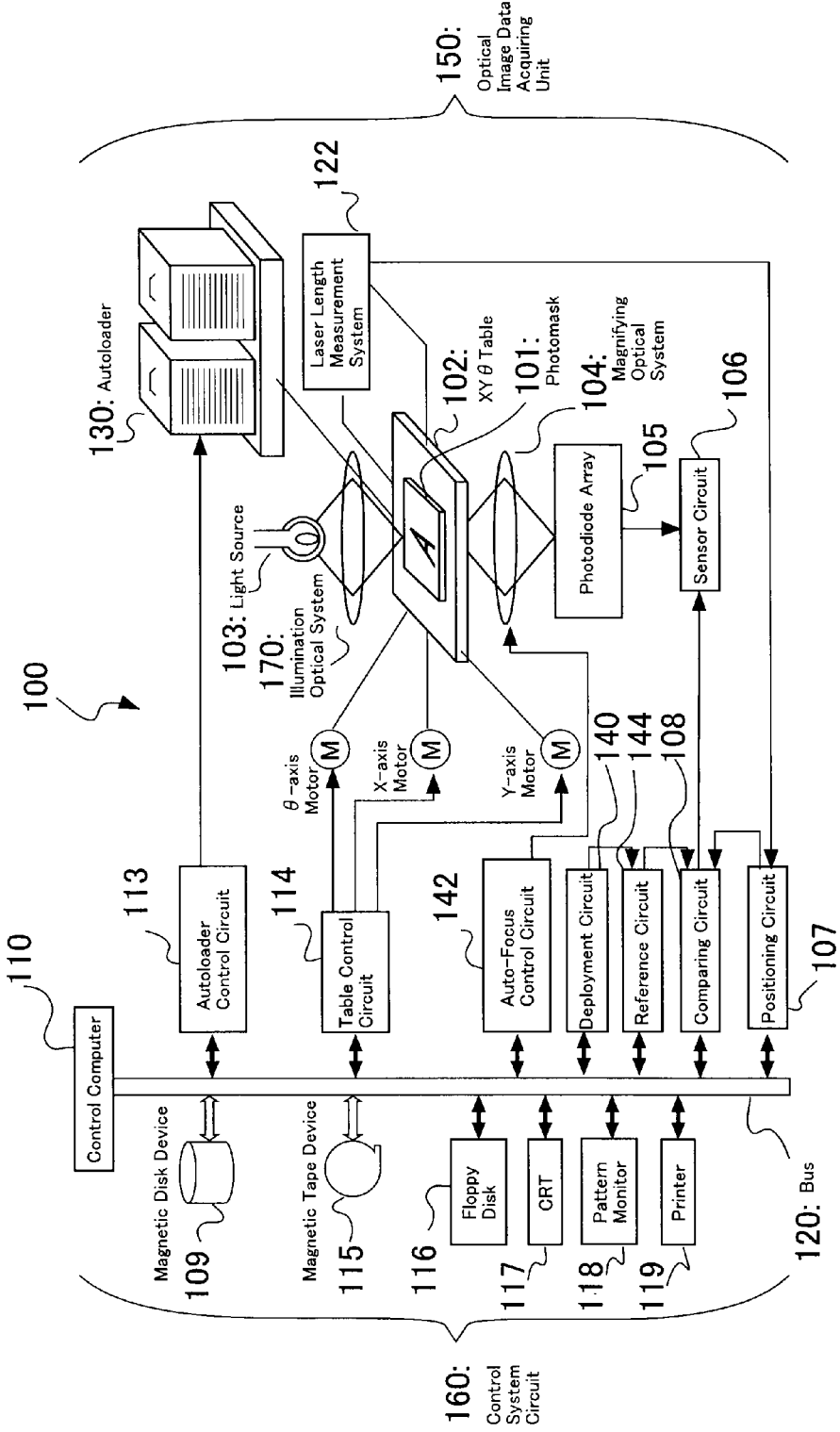
FIG. 2 is a diagram showing an overall configuration of the reticle defect inspection apparatus in the first embodiment.
Figure 3:
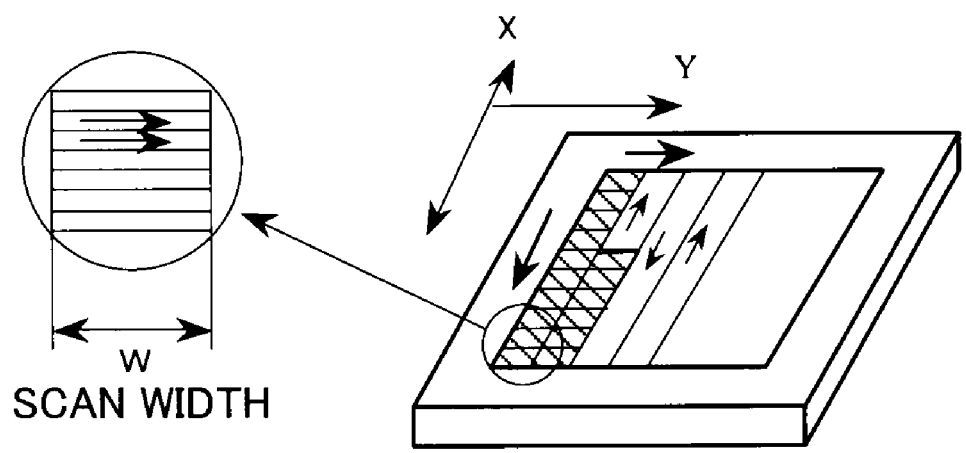
FIG. 3 is an explanatory view of inspection stripes of an inspected area in the first embodiment.

FIG. 2 is a diagram showing an overall configuration of the reticle defect inspection apparatus in the present embodiment. A reticle defect inspection apparatus 100 has an optical image data acquiring unit 150 and a control system circuit 160 for controlling the optical image data acquiring unit 150. In the reticle defect inspection apparatus 100, an inspected area in a pattern formed on a reticle 101, which is a measured sample, is virtually divided, as shown in FIG. 3, into inspection stripes in a strip shape having a width W. An inspection is carried out by putting the reticle (or photomask) 101 on an XYθ table 102 shown in FIG. 2 and continuously moving a uniaxial stage so that the divided inspection stripes are continuously operated. When an inspection of one stripe is completed, a step movement occurs to observe the next stripe.

The reticle 101 is put on the XYθ table 102 using an autoloader 130 and an autoloader control circuit 113. However, a pattern may not always be in parallel with a running axis of the table. Thus, the reticle 101 is in most cases fixed onto a rotatable θ stage so that the reticle 101 can be mounted in parallel with the running axis. The above XYθ table 102 is controlled by using an X-axis motor, a Y-axis motor, a θ-axis motor, and a table control circuit 114.

Moreover, the reticle defect inspection apparatus 100 has an illuminating optical system 170 for irradiating the reticle 101 with an inspection light and a magnifying optical system 104 for a pattern image of the reticle 101 irradiated with an inspection light. A pattern formed on the reticle 101 is irradiated via the illuminating optical system 170 with a light emitted from a suitable light source 103 as an inspection light. The light inspection that passes through the reticle is incident on a photodiode array 105, which is an imaging means for inspection, via the detecting optical system 104. A portion of a strip-shaped area of the virtually divided pattern shown in FIG. 3 is expanded on the photodiode array 105 before being formed as an optical image (pattern image). The magnifying optical system 104 is autofocus-controlled in order to maintain good image-forming conditions.

A pattern image formed on the photodiode array 105 undergoes a photoelectric conversion by the photodiode array 105 and further an A/D conversion by a sensor circuit 106. Measured image data output from the sensor circuit 106 is sent to a comparing circuit 108 together with data indicating the position of the reticle 101 on the XYθ table 102 output from a positioning circuit 107.

Design data used for pattern formation of the reticle 101, on the other hand, is read from a magnetic disk device 109 to a deployment circuit 140 via a control computer 110. The read design data is converted by the deployment circuit 140 into two-valued or multi-valued design image data, which is sent to a reference circuit 144. The reference circuit 144 performs suitable filter processing on the sent graphic design image data.

The filter processing is performed because a filter has acted on measured pattern data acquired from the sensor circuit 106 by resolution characteristics of the detecting optical system 104, an aperture effect of the photodiode array 105 or the like and thus, the filter processing is performed also on the design image data to adjust the design image data to the measured image data. The comparing circuit 108 compares the measured image data with the design image data on which suitable filter processing has been performed according to an appropriate algorithm and, if both pieces of data do not match, determines that the reticle is defective.

In a reticle inspection apparatus in the present embodiment for inspecting for defects or foreign matter existing in a pattern formed on the surface of a reticle, which is an inspected sample, a reticle pattern image is formed using an optical system similar to a high-resolution microscope. Then, the reticle pattern image is acquired as image information using, for example, a CCD camera like the aforementioned photodiode array or an imaging device such as a line sensor, and the image information is compared with a reference image acquired or formed separately to detect defects or foreign matter in the pattern.

Incidentally, a detailed configuration of an optical system of transmitted illumination, an optical system of reflected illumination, the detecting optical system and the like to realize a simultaneous inspection of transmission and reflection is not shown in FIG. 2. For realization of a simultaneous inspection of transmission and reflection, it is necessary to provide an optical system of transmitted illumination, an optical system of reflected illumination, and a corresponding detecting optical system, and further two systems of the comparing circuit 108 or the like for defect detection.

Figure 1:
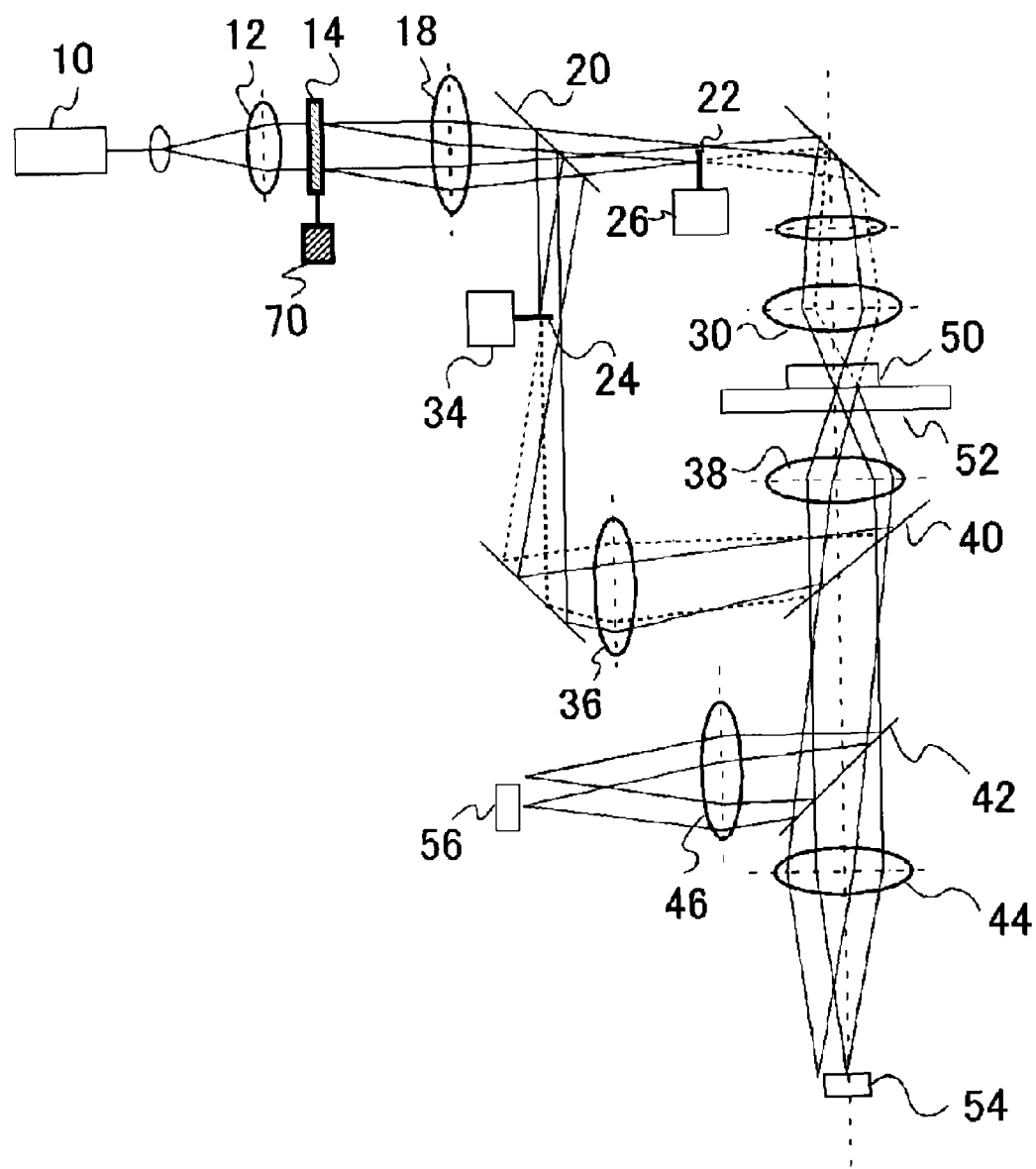
FIG. 1 is a diagram showing an optical system of a reticle defect inspection apparatus in a first embodiment.

FIG. 1 is a diagram showing an optical system of the reticle defect inspection apparatus in the present embodiment. Of the overall configuration diagram shown in FIG. 2, a portion corresponding to the light source 103, the positioning circuit 107, the reticle 101, the XYθ table 102, the magnifying optical system 104, the photodiode array 105, and the sensor circuit 106 is shown.

First, the optical system shown in FIG. 1 comprises, for example, a light source 10 emitting a laser light of the wavelength 199 nm. The illuminating optical system comprises a beam expander 12 for expanding a light emitted from the light source 10 and an integrator 14 for making illumination distribution of an inspection light uniform to make the light a surface light source. More specifically, a fly eye lens or a rod lens array can be used as the optical integrator 14.

Further, the illuminating optical system comprises a moving mechanism 70 for enabling the integrator 14 to move slightly in a direction perpendicular to the optical axis of the moving mechanism 70, in other words, in the perpendicular to an optical path. Here, slight movement is a movement within a range of distance between individual lenses, which are elements constituting the integrator 14. Therefore, considering the size of integrator used for reticle defect inspection, a movement within the range of generally several μm to several mm is herein called slight movement. As motive power of the moving mechanism 70, for example, a pulse motor or a piezoelectric element can be used. In addition, it is desirable that the integrator 14 be slightly movable in the X and Y directions, which are two directions perpendicular to each other on a surface perpendicular to the optical axis of the integrator 14. This is because, as will be described later, the degree of freedom of integrator movement will be thereby higher to prevent deterioration of optical components.

In addition, the illuminating optical system comprises a collimator 18 for making a light that passes through the integrator 14 parallel rays. A first beam splitter 20 has a function of splitting parallel rays that have passed through the collimator 18 into a transmitted illumination light, which is a first inspection light, and a reflected illumination light, which is a second inspection light. Here, an optical system from the first beam splitter 20 up to a reticle 50 which is irradiated with the transmitted illumination light, which is the first inspection light, is called an optical system of transmitted illumination. An optical system up to irradiation of the reticle 50 with the reflected illumination light, which is the second inspection light, is called an optical system of reflected illumination.

The optical system of transmitted illumination and the optical system of reflected illumination are each configured so that the transmitted illumination light and the reflected illumination light are provided as Koehler illumination at positions of a transmission field stop 22 and a reflection field stop 24 respectively. The position of the transmission field stop 22 is set in such a way that the position and a pattern surface of the reticle 50 are conjugate and an area regulated and illuminated by the transmission field stop 22 becomes a transmitted illumination area. A first pulse motor 26 for driving the transmission field stop 22 is also provided to set a viewing position. Moreover, a condenser lens 30 is arranged so that a light, after passing through the transmission field stop 22, is provided as Koehler illumination on the pattern surface of the reticle 50.

The position of the reflection field stop 24, on the other hand, is set in such a way that the position and the pattern surface of the reticle 50 are conjugate and an area regulated and illuminated by the reflection field stop 24 becomes a reflected illumination area. A third pulse motor 34 for driving the reflection field stop 24 is provided to set a viewing position. Moreover, a collimator 36 and an objective lens 38 are also arranged so that a light, after passing through the reflection field stop 24, is provided as Koehler illumination on the pattern surface of the reticle 50. A second beam splitter 40 is provided between the collimator 36 and the objective lens 38 to introduce a reflected illumination light onto the pattern surface.

In addition, the reticle defect inspection apparatus in the present invention has a detecting optical system that can simultaneously detect a transmitted light obtained by irradiation of the reticle 50 with the first inspection light and a reflected light obtained by irradiation of the sample with the second inspection light. First, the objective lens 38 for condensing both the transmitted light and reflected light is provided as a component of the detecting optical system. Further, a third beam splitter 42 for separating the light condensed by the objective lens 38 into a transmitted light and a reflected light is provided. Also, a first image-forming optical system 44 for forming an image of the transmitted light separated by the third beam splitter 42 and a second image-forming optical system 46 for forming an image of the reflected light separated by the third beam splitter 42 are provided.

Further, the reticle defect inspection apparatus in the present invention comprises a first imaging sensor 54, which is an imaging means for inspection of pattern images by the transmitted light whose image is formed by the first image-forming optical system 44, and a second imaging sensor 56, which is an imaging means for inspection of pattern images by the reflected light whose image is formed by the second image-forming optical system 46 are provided.

In the configuration of the above optical system, a luminescent spot surface formed by the integrator 14 forming uniform illumination may be formed at a position of an optical component. For example, a light, after being passed through the integrator 14, is split into a transmitted illumination light, which is the first inspection light, and a reflected illumination light, which is the second inspection light, and a luminescent spot surface formed by both these inspection lights is formed at a pupil position of the optical system of the objective lens 38. Then, if the objective lens 38 physically exists at the pupil position of the optical system, as described above, the objective lens deteriorates due to energy of luminescent spots. Thus, correct optical images cannot be obtained, leading to lower inspection precision of the reticle defect inspection apparatus.

Incidentally, the position of the luminescent spot surface formed in an optical system, luminescent spot sizes, numbers, intervals, and the like are determined by various parameters of the optical system used, for example, the wavelengths of the light source, numbers and sizes of various element lenses of the integrator, NA of the lenses and the like.

According to the reticle defect inspection apparatus in the present embodiment described above, the integrator 14 can be moved by driving the moving mechanism 70 even if a luminescent spot surface exists in an optical component such as the objective lens 38. Accordingly, light fluxes emitted from the integrator can be moved to move the position of luminescent spots in the optical component. Therefore, it becomes possible to avoid concentration of energy on the same position of the optical component for a long time to suppress deterioration of the optical component. Thus, a reticle defect inspection apparatus that can sustain a defect inspection with high precision for a long time can be provided.

Figure 5:
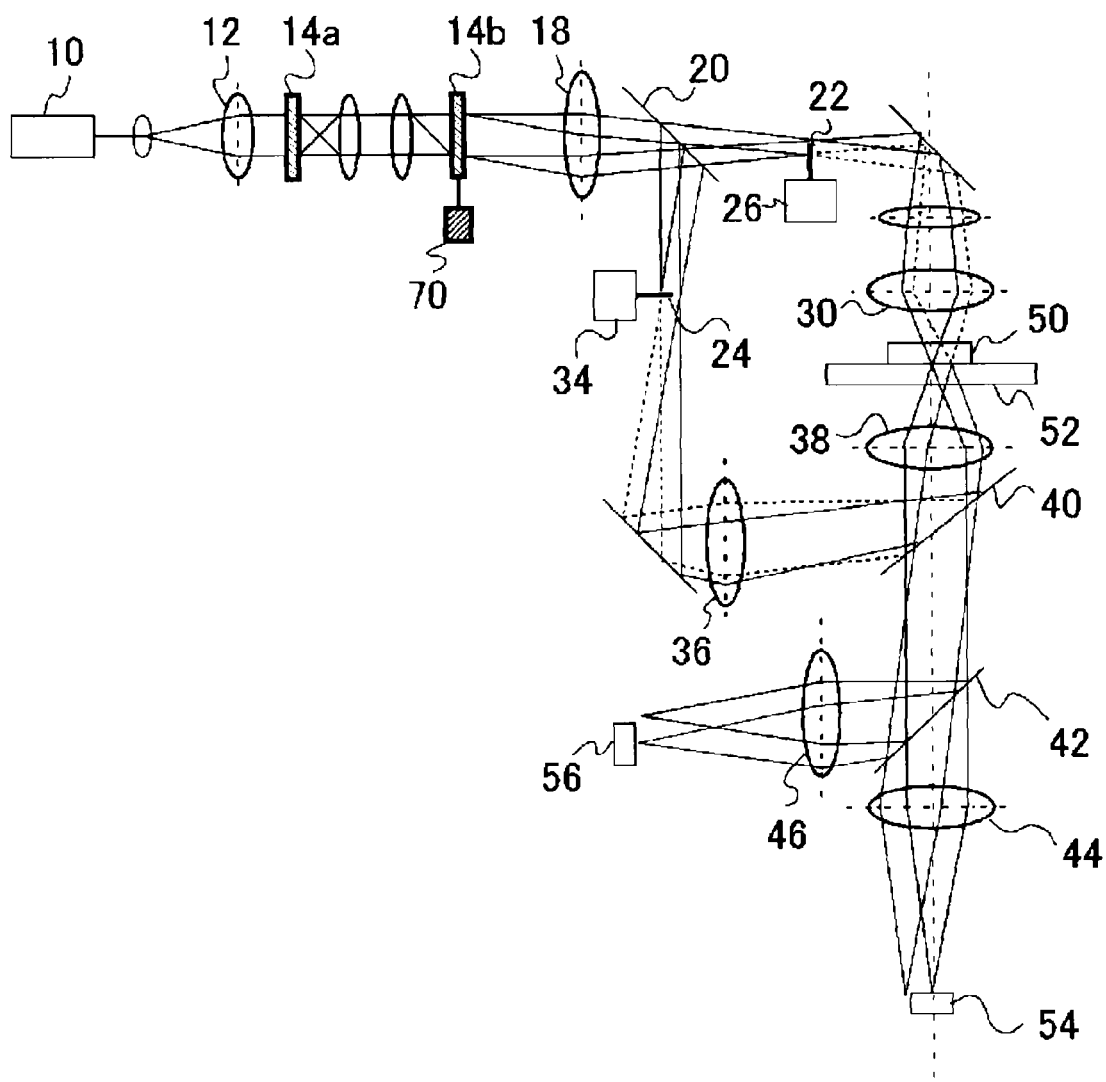
FIG. 5 is a diagram showing an optical system of a reticle defect inspection apparatus in a modification of the first embodiment.

Here, a case in which there is one integrator 14 has been described. However, as shown in a modification shown in FIG. 5, two integrators, a first-stage integrator 14a and a second-stage integrator 14b, may be provided to enhance uniformity of illumination distribution of inspection light. In this case, as shown, for example, in FIG. 5, an operation effect similar to that when there is one integrator can be gained by providing the moving mechanism 70 for the second-stage integrator 14b. Incidentally, in this case, the moving mechanism may be provided only for the first-stage integrator 14a or both the first-stage integrator 14a and the second-stage integrator 14b.

Next, an inspection method using a reticle defect inspection apparatus in the present embodiment will be described.

The inspection method in the present embodiment has moving the integrator by a predetermined amount in the direction perpendicular to the optical axis of the integrator when the irradiation time of an inspection light exceeds a predetermined time.

For example, a reticle defect inspection of the reticle 101 is performed by an inspection light generated by the illuminating optical system 170 using the reticle defect inspection apparatus shown in FIG. 2. Such a reticle defect inspection is repeated a plurality of times and, if the added irradiation time of inspection light exceeds the predetermined time, the integrator 14 (FIG. 1) moves to prevent deterioration of any optical component in which a luminescent spot surface is present. Here, the predetermined time is determined by collectively considering the wavelengths of the light source, energy intensity at luminescent spots determined by the configuration of the integrator, resistance to deterioration of an optical component determined by material and the like of the optical component, degree of deterioration permitted for the optical component and the like.

Though, here, the integrator is moved based on the added amount of irradiation time, the integrator may also be moved simply based on the number of times of reticle defect inspections performed, the number of operation days, or the like to facilitate management.

Moreover, the integrator is moved by the predetermined amount in the direction perpendicular to the optical axis of the integrator. Here, the direction perpendicular to the optical axis of the integrator is a direction, if referred to FIG. 1, on a plane perpendicular to the page space. By moving the integrator in the direction perpendicular to the optical axis of the integrator, luminescent spots inside an optical component will most effectively be moved in view of the movement amount of the integrator. Shifts from the perpendicular direction due to machine errors or the like are included herein in the concept of the perpendicular direction.

The predetermined amount of movement is also determined by collectively considering the wavelengths of the light source, energy intensity at luminescent spots determined by the configuration of the integrator, luminescent spot sizes, resistance to deterioration of an optical component determined by material and the like of the optical component, degree of deterioration permitted for the optical component and the like.

Next, a concrete example of a method of moving the integrator will be described using FIGS. 1 and 4. Here, a laser light of wavelength 199 nm is assumed as a light source. A light emitted from the light source 10 passes through the integrator 14 (FIG. 1) before being split by the first beam splitter 20. Then, one split light passes through the optical system of transmitted illumination such as the condenser lens 30 and then transmits through the reticle 50 as a transmitted illumination light before reaching the objective lens 38. The other light passes through the optical system of reflected illumination such as the second beam splitter 40 before being incident on the objective lens 38 as a reflected illumination light.

In this configuration example, a luminescent spot surface by the integrator 14 is formed at the pupil position of the objective lens 38 where the lens is physically present for both the transmitted illumination light and reflected illumination light. Then, the interval between luminescent spots is, for example, 200 μm.

Figure 4:
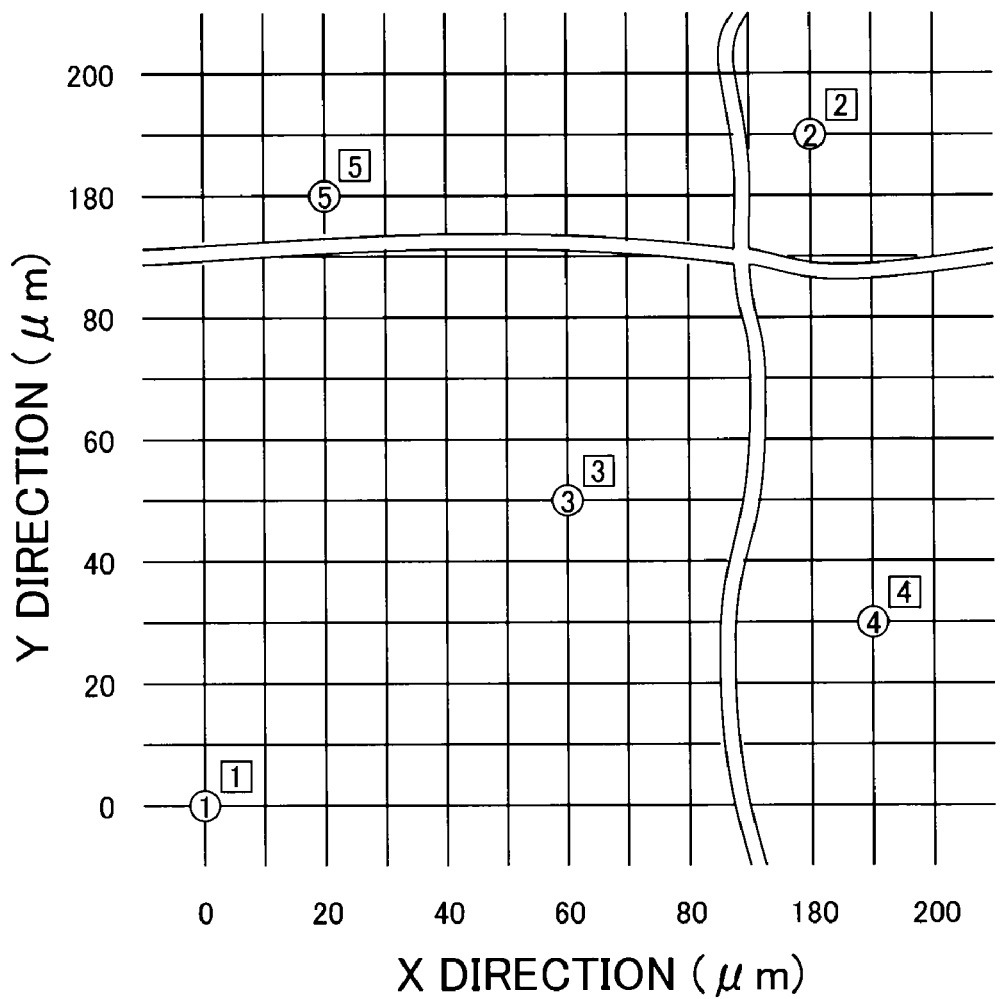
FIG. 4 is a diagram showing a method of moving luminescent spots on a luminescent spot surface in an objective lens in the first embodiment.

FIG. 4 shows the method of moving luminescent spots on a luminescent spot surface in the objective lens. FIG. 4 cuts out a portion of the luminescent spot surface. First, before moving luminescent spots, luminescent spots are present at positions (0, 0), (0, 200), (200, 0) and (200, 200) in the XY coordinate axes shown in FIG. 4. Then, to indicate the amounts of movement and movement positions of luminescent spots hereafter, numbers are denoted with reference to the luminescent spot at position (0, 0). The luminescent spot before movement is indicated by circled 1 (denoted by the circled number 1 in FIG. 4).

If, for example, the diameter of one luminescent spot is 10 μm, it is desirable that the luminescent spot move at least 10 μm in the next movement of the luminescent spot so that the luminescent spot should not overlap with the previous luminescent spot. That is, it is desirable that the integrator be moved by an amount required for making movement of the luminescent spot on the luminescent spot surface at least 10 μm so that irradiation areas before and after the movement should not overlap. If the amount of movement is assumed to be 10 μm, 200/10=20 movement points can be reserved for each of the X and Y directions, as shown by the grids in FIG. 4, when the interval between luminescent spots is 200 μm. Thus, movement of 20×20=400 points (400 times) becomes possible without overlapping with a position once irradiated with a luminescent spot. That is, if a movement is made once a day or so, conditions in which the same luminescent spot position does not occur for more than one year can be created.

Moreover, the integrator may be moved successively in the X or Y direction so that the luminescent spot is moved by 10 μm at a time. However, as shown in FIG. 4, it is desirable that the integrator be moved randomly (however, the same position is not used) for each movement like circled 2, circled 3, circled 4, circled 5 . . . after circled 1. That is, it is desirable that the integrator be moved without specific regularity. This is because it becomes possible to equalize deterioration on a plane by making the movement random even if an optical component slightly deteriorates due to luminescent spot irradiation.

Further, in order to extend life of optical components to enable a defect inspection with high precision for a long time, it is also effective, after the first cycle of 400-times movement, to further make 400-times movement in the second cycle at positions shifted by, for example, half the diameter of the luminescent spot, that is, 5 μm (denoted by squared numbers in FIG. 4).

According to the reticle defect inspection method in the present embodiment described above, concentration of energy on the same position of an optical component for a long time can be avoided so that deterioration of the optical component can be suppressed. Thus, a reticle defect inspection method that can sustain a defect inspection with high precision for a long time can be provided.

Here, in the present embodiment, a case in which a luminescent spot surface is formed at the optical pupil position of an objective lens has principally been described. However, the present embodiment has a similar operation effect if, for example, a luminescent spot surface is formed at the optical pupil position of a rescalable lens or inside other optical components such as a splitter or a mirror.

Second Embodiment

A reticle defect inspection apparatus in the present embodiment has an optically transparent optical path change plate provided on an optical path on the side of reticle of the integrator, instead of the moving mechanism of the integrator. Since the present embodiment is the same as the first embodiment except that a moving mechanism that can tilt the optical path change plate with respect to the optical axis of the integrator is provided, a duplicated description is omitted.

Figure 6:
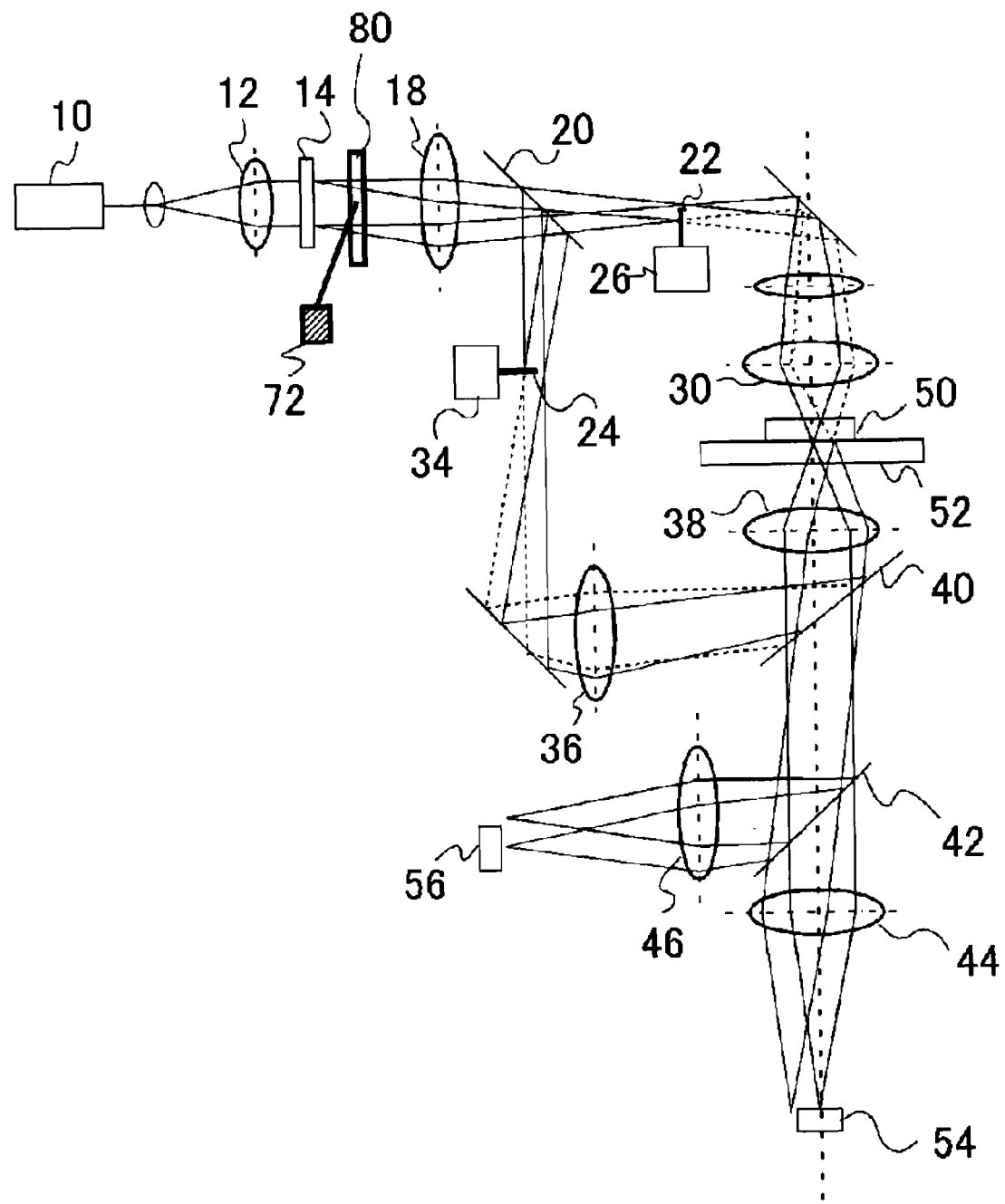
FIG. 6 is a diagram showing an optical system of a reticle defect inspection apparatus in a second embodiment.

FIG. 6 is a diagram showing an optical system of a reticle defect inspection apparatus in the present embodiment. In the reticle defect inspection apparatus in the present embodiment, as shown in FIG. 6, an optically transparent optical path change plate 80 composed of, for example, a transparent quarts glass plate is provided on an optical path between the integrator 14 and the collimator 18, that is, on an optical path on the side of reticle with respect to the integrator. Moreover, a moving mechanism 72 that enables the optical path change plate 80 to tilt with respect to the optical axis of the integrator is provided.

As motive power of the moving mechanism 72, for example, a pulse motor or a piezoelectric element can be applied.

Figure 7:
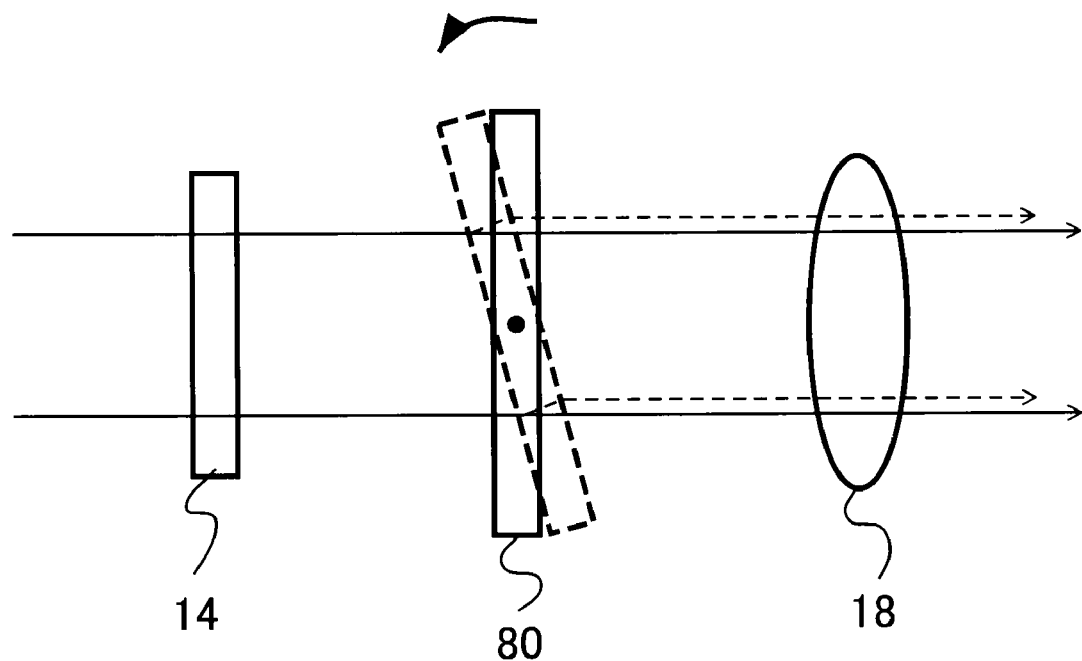
FIG. 7 is a diagram showing an operation of the reticle defect inspection apparatus in the second embodiment.

FIG. 7 is a diagram for illustrating an operation of the present embodiment. If, as shown in FIG. 7, the optical path change plate 80 is tilted with respect to the optical axis of the integrator 14, the optical path is changed due to refraction when light is incident on and emitted from the optical path change plate 80. That is, an optical path after tilting indicated by broken line arrows is shifted in parallel with respect to that before the optical path change plate 80 being tilted indicated by solid line arrows.

Also in the present embodiment, as described above, like the first embodiment, positions of formed luminescent spots can be moved by moving light fluxes emitted from the integrator. Therefore, an operation effect similar to that of the first embodiment can be gained.

Incidentally, movement of luminescent spots can be controlled by material, thickness, the amount of tilting, and the like of the optical path change plate 80.

Here, a case in which there is one optical path change plate 80 has been described. If there is one optical path change plate 80, it is difficult to move luminescent spots on a luminescent spot surface in both the X and Y directions. Thus, it is also possible to successively provide two optical path change plates 80 and to tilt each of the two optical path change plates 80 in different directions so that luminescent spots can be moved in both the X and Y directions.

Embodiments of the present invention have been described above with reference to concrete examples. Though a description of components that are not directly needed for describing the present invention such as a reticle defect inspection apparatus and a reticle defect inspection method is omitted in descriptions of the embodiments, components needed for a reticle defect inspection apparatus or a reticle defect inspection method can suitably be selected and used.

In addition, all reticle defect inspection apparatuses and reticle defect inspection methods having components of the present invention and whose design can suitably be modified by a person skilled in the art are included in the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A reticle defect inspection apparatus, comprising:
an illuminating optical system of reflected illumination for irradiating a reticle with an inspection light and
a detecting optical system for detecting a pattern image of the reticle irradiated with the inspection light, the pattern image being formed by the inspection light reflected by the reticle, wherein
the illuminating optical system includes:
an integrator for equalizing illumination distribution of the inspection light; and
a moving mechanism for enabling the integrator to move in a direction perpendicular to an optical axis of the integrator,
wherein the moving mechanism is configured to move the integrator after a reticle defect inspection is repeated a plurality of times and when added irradiation time of inspection light exceeds a predetermined time.

2. The apparatus according to claim 1, wherein the moving mechanism has a function to move the integrator in two directions perpendicular to each other.

3. The apparatus according to claim 1, wherein the moving mechanism is configured to move the integrator so that the same luminescent spot position does not occur in an objective lens.

4. A reticle defect inspection apparatus, comprising:
an illuminating optical system of reflected illumination for irradiating a reticle with an inspection light, the pattern image being formed by the inspection light reflected by the reticle, and
a detecting optical system for detecting a pattern image of the reticle irradiated with the inspection light, wherein
the illuminating optical system includes:
an integrator for equalizing illumination distribution of the inspection light;
an optically transparent optical path change plate provided on an optical path on a side of the reticle of the integrator; and
a moving mechanism for enabling the optical path change plate to tilt with respect to an optical axis of the integrator,
wherein the moving mechanism is configured to move the optical path change plate after a reticle defect inspection is repeated a plurality of times and when added irradiation time of inspection light exceeds a predetermined time.

5. The apparatus according to claim 4, wherein the optical path change plate is a transparent quarts glass plate.

6. The apparatus according to claim 4, wherein the moving mechanism is configured to move the optical path change plate so that the same luminescent spot position does not occur in an objective lens.

7. An inspection method using a reticle defect inspection apparatus, wherein
the reticle defect inspection apparatus comprises:
an illuminating optical system of reflected illumination for irradiating the reticle with an inspection light; and
a detecting optical system for detecting a pattern image of the reticle irradiated with the inspection light, the pattern image being formed by the inspection light reflected by the reticle,
the illuminating optical system includes:
an integrator for equalizing illumination distribution of the inspection light; and
a moving mechanism for enabling the integrator to slightly move in a direction perpendicular to an optical axis of the integrator, and
the integrator is moved in the direction perpendicular to the optical axis of the integrator after a plurality of reticle defect inspections have been performed and if added irradiation time of inspection light exceeds a predetermined time.

8. The method according to claim 7, wherein after the integrator is moved, the reticle defect inspection is further continued to repeat the movement of the integrator, the integrator is moved in a random direction and by a random distance for each time of the movement.

* * * * *